(12) United States Patent
Shimamoto et al.

(10) Patent No.: US 11,054,565 B2
(45) Date of Patent: Jul. 6, 2021

(54) OPTICAL FIBER SCANNING APPARATUS FOR ADJUSTING A DRIVING FREQUENCY OF THE OPTICAL FIBER

(71) Applicant: OLYMPUS CORPORATION, Tokyo (JP)

(72) Inventors: Atsuyoshi Shimamoto, Tokyo (JP); Soichiro Koshika, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 451 days.

(21) Appl. No.: 16/101,551

(22) Filed: Aug. 13, 2018

(65) Prior Publication Data

US 2019/0004233 A1    Jan. 3, 2019

Related U.S. Application Data

(63) Continuation of application No. PCT/JP2016/059363, filed on Mar. 24, 2016.

(51) Int. Cl.
| | |
|---|---|
| *A61B 1/00* | (2006.01) |
| *G02B 26/10* | (2006.01) |
| *G02B 6/00* | (2006.01) |
| *F21V 8/00* | (2006.01) |
| *G02B 23/24* | (2006.01) |

(52) U.S. Cl.
CPC ........ *G02B 6/0008* (2013.01); *A61B 1/00006* (2013.01); *A61B 1/00172* (2013.01); *G02B 23/24* (2013.01); *G02B 26/103* (2013.01); *G02B 2006/0098* (2013.01)

(58) Field of Classification Search
None
See application file for complete search history.

(56) References Cited

U.S. PATENT DOCUMENTS

2009/0062659 A1*   3/2009   Weir ................. A61B 1/00096
                                                          600/476
2014/0114131 A1*   4/2014   Sakai .................. G02B 26/103
                                                          600/182
(Continued)

FOREIGN PATENT DOCUMENTS

EP             3108794 A1    12/2016
JP          2008-514342 A     5/2008
(Continued)

OTHER PUBLICATIONS

International Search Report dated Jun. 14, 2016 issued in PCT/JP2016/059363.

*Primary Examiner* — John P Leubecker
(74) *Attorney, Agent, or Firm* — Scully, Scott, Murphy & Presser, P.C.

(57) ABSTRACT

An optical scanning apparatus including: an optical fiber that is configured to guide light from a light source to emit the light from a distal end thereof; a driver that is configured to oscillate the distal end of the optical fiber at a driving frequency in a direction intersecting a longitudinal axis of the optical fiber; a resonance-frequency detector that is configured to detect a resonance frequency of the distal end of the optical fiber; and a driving-frequency adjustor that is configured to adjust the driving frequency so that the ratio between the resonance frequency detected by the resonance-frequency detector and the driving frequency becomes constant.

4 Claims, 9 Drawing Sheets

(56) References Cited

U.S. PATENT DOCUMENTS

| | | | |
|---|---|---|---|
| 2014/0236022 A1* | 8/2014 | Zeng | A61B 1/0125 |
| | | | 600/476 |
| 2015/0338646 A1* | 11/2015 | Innami | A61B 1/00172 |
| | | | 359/213.1 |
| 2016/0150948 A1 | 6/2016 | Shimamoto | |
| 2016/0324403 A1* | 11/2016 | Yeoh | H01L 41/042 |
| 2017/0045734 A1* | 2/2017 | Shimamoto | A61B 1/00172 |
| 2017/0071455 A1* | 3/2017 | Shimamoto | A61B 1/00172 |
| 2018/0064323 A1* | 3/2018 | Fujinuma | A61B 1/00096 |
| 2018/0136455 A1* | 5/2018 | Fujinuma | G02B 23/2469 |
| 2018/0196250 A1* | 7/2018 | Shimamoto | G02B 23/2469 |

FOREIGN PATENT DOCUMENTS

| | | | |
|---|---|---|---|
| JP | 2014198089 A | * | 10/2014 |
| JP | 2015-075685 A | | 4/2015 |
| WO | WO 2006/041452 A1 | | 4/2006 |
| WO | WO 2014/188719 A1 | | 11/2014 |
| WO | WO 2015/125976 A1 | | 8/2015 |

\* cited by examiner

OPTICAL FIBER SCANNING APPARATUS FOR ADJUSTING A DRIVING FREQUENCY OF THE OPTICAL FIBER

CROSS-REFERENCE TO RELATED APPLICATIONS

This is a Continuation Application of International Application No. PCT/JP2016/059363 filed on Mar. 24, 2016, the content of which is incorporated herein by reference in its entirety.

TECHNICAL FIELD

The present invention relates to an optical scanning apparatus.

BACKGROUND ART

There is a known scanning endoscope that obtains an image by oscillating, by means of resonance, an emission end of an optical fiber that guides light from a light source, two-dimensionally scanning light emitted from the emission end on an imaging subject, and receiving light returning from each scanning position on the imaging subject (for example, see Patent Literature 1).

In this scanning endoscope, image distortion is corrected by obtaining coordinate values of a scanning trajectory in advance by using a scanning-position detection device, such as a PSD (Position Sensor Device), and assigning the obtained coordinate values to pixels in the form of a lookup table.

CITATION LIST

Patent Literature

{PTL 1} Japanese Translation of PCT International Application, Publication No. 2008-514342

SUMMARY OF INVENTION

An aspect of the present disclosure is an optical scanning apparatus including: an optical fiber configured to guide light from a light source to emit the light from a distal end thereof; a driver that is configured to oscillate the distal end of the optical fiber at a driving frequency in a direction intersecting a longitudinal axis of the optical fiber; a resonance-frequency detector that is configured to detect a resonance frequency of the distal end of the optical fiber; and a driving-frequency adjustor that is configured to adjust the driving frequency so that the ratio between the resonance frequency detected by the resonance-frequency detector and the driving frequency becomes constant.

Another aspect of the present disclosure is an optical scanning apparatus including: an optical fiber that is configured to guide light from a light source to emit the light from a distal end thereof; a driver that is configured to oscillate the distal end of the optical fiber at a driving frequency in a direction intersecting a longitudinal axis of the optical fiber; a resonance-frequency detector that is configured to detect a resonance frequency of the distal end of the optical fiber; a driving-frequency adjustor that is configured to adjust the driving frequency; and a memory that is configured to store a reference resonance frequency and a reference driving frequency, which are set in advance, or the value of a ratio thereof, wherein the driving-frequency adjustor is configured to adjust the driving frequency so that the ratio between the resonance frequency detected by the resonance-frequency detector and the driving frequency becomes equal to the value of the ratio stored in the memory.

DESCRIPTION OF EMBODIMENTS

A scanning endoscope 1 according to an embodiment of the present invention will be described below with reference to the drawings.

Figure 1:
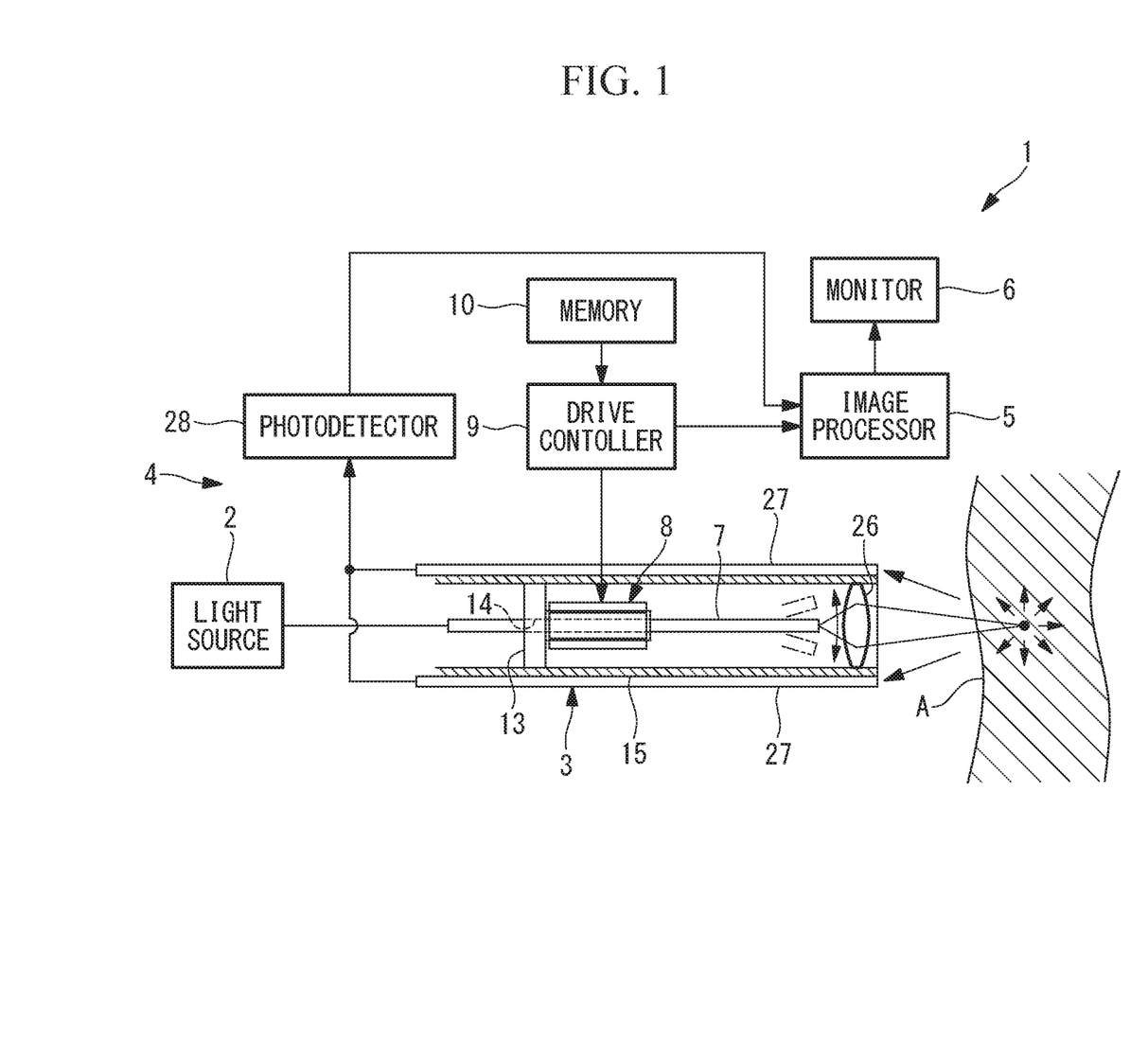
FIG. 1 is an overall configuration diagram showing a scanning endoscope according to an embodiment of the present invention.

As shown in FIG. 1, the scanning endoscope 1 according to this embodiment is provided with: an optical scanning apparatus 3 according to an embodiment of the present invention, which scans illumination light (for example, excitation light) from a light source 2 on an imaging subject A; a light detection unit 4 that detects light (for example, light reflected at the surface of the imaging subject A or fluorescence) generated at the imaging subject A; an image processing unit (image generation unit) 5 that generates an image of the imaging subject A on the basis of the intensity of the light detected by the light detection unit 4; and a monitor 6 that displays the generated image.

The optical scanning apparatus 3 according to this embodiment is provided with: an optical fiber 7 that guides the illumination light from the light source 2 and that emits the illumination light from a distal end thereof; a drive unit 8 that causes the distal end of the optical fiber 7 to oscillate in a direction orthogonal to a longitudinal axis of the optical fiber 7; and a drive control unit 9 that controls the drive unit 8. In addition, the optical scanning apparatus 3 according to this embodiment is provided with a storage unit 10 that individually stores a resonance frequency (reference resonance frequency) of the distal end of the optical fiber 7 and a driving frequency (reference driving frequency) at which the drive unit 8 is driven, the frequencies being adjusted to the state at the time of factory shipment or when the apparatus is set up.

Figure 2:
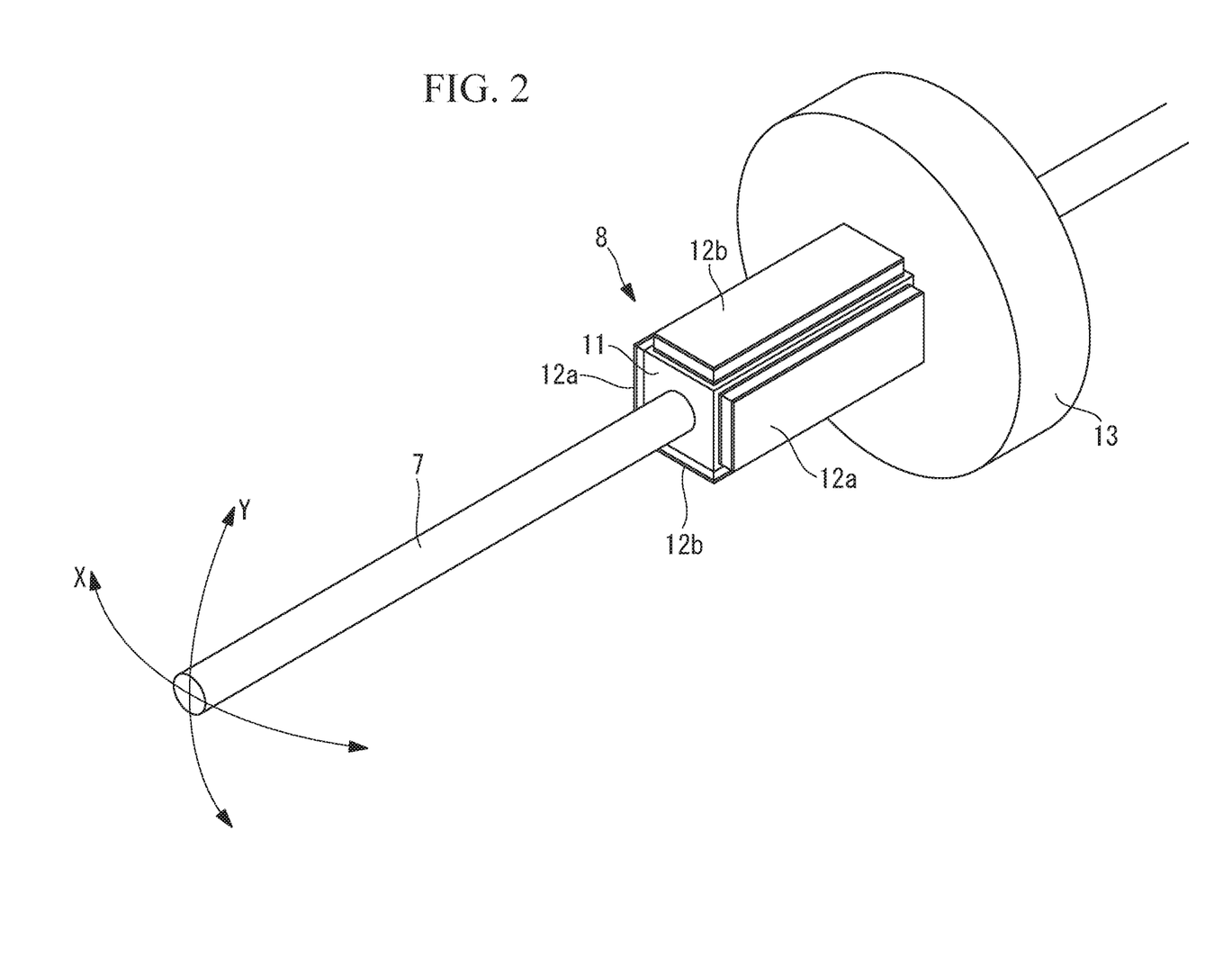
FIG. 2 is a perspective view showing an optical scanning apparatus according to an embodiment of the present invention, provided in the scanning endoscope in FIG. 1.

As shown in FIG. 2, the drive unit 8 is provided with: a tubular vibration transmission member 11 that supports the optical fiber 7, at a position away from the distal end of the optical fiber 7 by a prescribed distance, in a state in which the optical fiber 7 is made to penetrate therethrough; and four piezoelectric elements 12a, 12b that are adhered to outer surfaces of the vibration transmission member 11 at equal intervals in the circumferential direction.

The vibration transmission member 11 is formed of a conductive metal material and, as shown in FIG. 1, has a shape in which a through-hole 14 through which the optical fiber 7 can penetrate is formed along a longitudinal axis of a square column having a circular flange part 13 at one end thereof, and is fixed to an outer cylinder member 15 by means of the flange part 13.

Each of the piezoelectric elements 12a, 12b is formed in a flat-plate shape in which electrodes are provided on both end surfaces in the thickness direction, and is fixed in a state in which one of the electrodes is electrically in contact with the respective side surface of the square column portion of the vibration transmission member 11. The two pairs of piezoelectric elements 12a, 12b arranged at opposing positions with the optical fiber 7 interposed therebetween are arranged such that the polarization directions of each pair are oriented in the same direction. Alternating voltages of the same phase are supplied to the piezoelectric elements 12a, 12b arranged at the opposing positions with the optical fiber 7 interposed therebetween.

Figure 3:
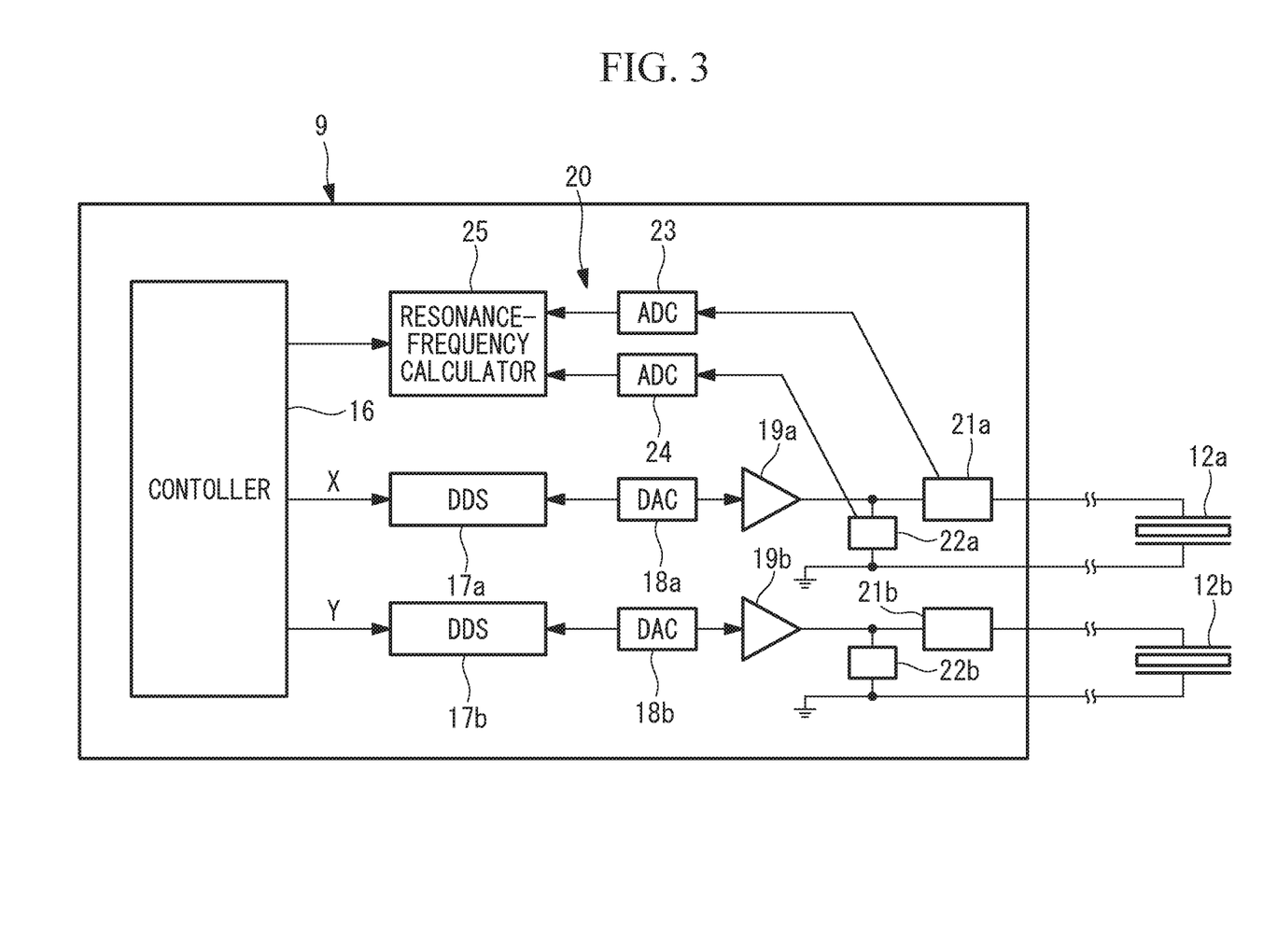
FIG. 3 is a block diagram for explaining a drive controller provided in the optical scanning apparatus in FIG. 2.

As shown in FIG. 3, the drive control unit 9 is provided with: a control unit (driving-frequency adjustment unit) 16 that outputs control signals; DDSs (direct digital synthesizers) 17a, 17b for driving the piezoelectric elements 12a, 12b of the drive unit 8; DACs (digital-analog converters) 18a, 18b; and amplifiers 19a, 19b. The individual DDSs 17a, 17b respectively receive the control signals from the control unit 16 and generate digital drive signals. These digital drive signals are converted into analog signals by the DACs 18a, 18b and the converted signals are amplified by the amplifiers 19a, 19b, thereby driving the piezoelectric elements 12a, 12b.

In addition, the drive control unit 9 is provided with a resonance-frequency detection unit 20 that detects a resonance frequency of the distal end of the optical fiber 7.

The resonance-frequency detection unit 20 is provided with: a current detection circuit 21a and a voltage detection circuit 22a that are provided on a circuit from the amplifier 19a toward the piezoelectric element 12a; ADCs (analog-digital converters) 23, 24 that convert a current signal and a voltage signal detected by these circuits 21a, 22a into digital signals; and a resonance-frequency calculation unit 25 that calculates a resonance frequency of an X-direction oscillation (described later) on the basis of a phase difference between two outputs from the ADCs 23, 24. Similarly, for a resonance frequency of a Y-direction oscillation (described later), a current detection circuit 21b, a voltage detection circuit 22b, and ADCs 23, 24 (not shown) are provided on a circuit from the amplifier 19b toward the piezoelectric element 12b.

The resonance-frequency detection unit 20 detects the resonance frequencies of the oscillations of the optical fiber 7 at an appropriate timing, such as when activating the scanning endoscope 1.

In addition, the drive control unit 9 applies, to the two pairs of piezoelectric elements 12a, 12b, the alternating voltage oscillated at the driving frequency while changing the amplitude thereof in a sinusoidal wave form and shifting the phase by 90°. By doing so, the two pairs of piezoelectric elements 12a, 12b drive the optical fiber 7 in two directions (X-direction and Y-direction) orthogonal to each other.

Figure 4:
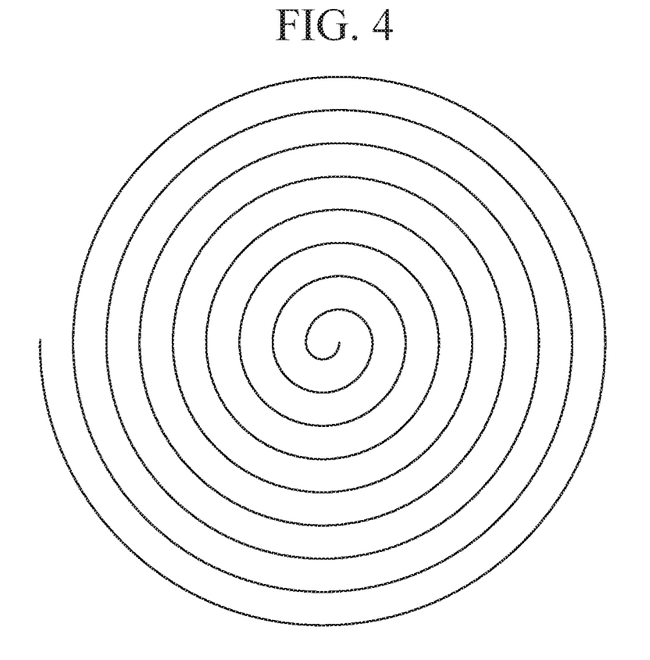
FIG. 4 is a diagram showing an example of an illumination-light scanning trajectory generated by the optical scanning apparatus in FIG. 2.

In other words, by applying the alternating voltage to the respective pairs of piezoelectric elements 12a, 12b, the optical fiber 7 is bent in the two directions orthogonal to each other due to bending vibrations of the respective pairs of piezoelectric elements 12a, 12b, and thereby, the distal end of the optical fiber 7 is displaced in a spiral manner, as shown in FIG. 4, and the illumination light emitted from the distal end of the optical fiber 7 is scanned in a spiral manner.

In FIG. 1, reference sign 26 indicates a focusing lens. The optical fiber 7 is, for example, a single-mode fiber.

In addition, the drive control unit 9 transmits information indicating scanning positions of the illumination light to the image processing unit 5.

The light detection unit 4 is provided with: at least one light-receiving optical fiber 27 that receives, at a distal end thereof, the light generated at the imaging subject A; and a photodetector 28, such as a photomultiplier tube, that detects the light received by the light-receiving optical fiber 27.

In this embodiment, a plurality of the light-receiving optical fibers 27 of the light detection unit 4 are arranged on the outside of the outer cylinder member 15, so as to be arrayed in the circumferential direction. The light-receiving optical fibers 27 are, for example, multi-mode fibers.

The image processing unit 5 generates an image by associating each position at which the illumination light is scanned by the optical scanning apparatus 3 with the intensity of the light detected by the photodetector 28 when the illumination light is radiated onto each of the scanning positions. The generated image is displayed on the monitor 6.

In the optical scanning apparatus 3 according to this embodiment, the control unit 16 of the drive control unit 9 calculates a driving frequency on the basis of the resonance frequency calculated by the resonance-frequency calculation unit 25 and the reference resonance frequency and the reference driving frequency that are stored in the storage unit 10. The control unit 16 calculates the driving frequency so that the ratio between the detected resonance frequency and the driving frequency matches the ratio between the reference resonance frequency and the reference driving frequency.

The operation of the thus-configured optical scanning apparatus 3 and scanning endoscope 1 according to this embodiment will be described below.

To observe tissue A inside the body of a patient by using the scanning endoscope 1 according to this embodiment, as shown in FIG. 1, the distal end of the scanning endoscope 1 is inserted into the body so as to face the tissue (imaging subject) A to be observed.

In this state, the illumination light is generated by the light source 2, and the drive control unit 9 drives the drive unit 8. By doing so, the illumination light from the light source 2, which is guided by the optical fiber 7, is emitted from the distal end of the optical fiber 7 toward the tissue A and is scanned, for example, in a spiral manner due to the oscillations of the distal end of the optical fiber 7.

By scanning the illumination light, although the light generated at each scanning position on the tissue A scatters in all directions, a portion of backscattered light that returns upon being scattered in the tissue A is received by the distal ends of the light-receiving optical fibers 27 of the light detection unit 4, and the intensity thereof is detected by the photodetector 28. The light detected by the photodetector 28 is transmitted to the image processing unit 5. Since the information indicating the scanning positions of the illumination light has been transmitted from the drive control unit 9 to the image processing unit 5, an image is generated by storing the intensity of the light detected by the photodetector 28 and the information indicating the scanning positions in association with each other. The generated image is displayed on the monitor 6.

In this case, with the scanning endoscope 1 according to this embodiment, the resonance-frequency detection unit 20 detects the resonance frequency at an appropriate timing, such as at the time of activation, and the control unit 16 adjusts the driving frequency on the basis of the detected resonance frequency. Therefore, even when the resonance frequency of the distal end of the optical fiber 7 fluctuates due to changes in the usage environment, such as temperature, and a temperature rise caused by sterilization treatment or the like, an appropriate driving frequency is set on the basis of the fluctuated resonance frequency.

Figure 5:
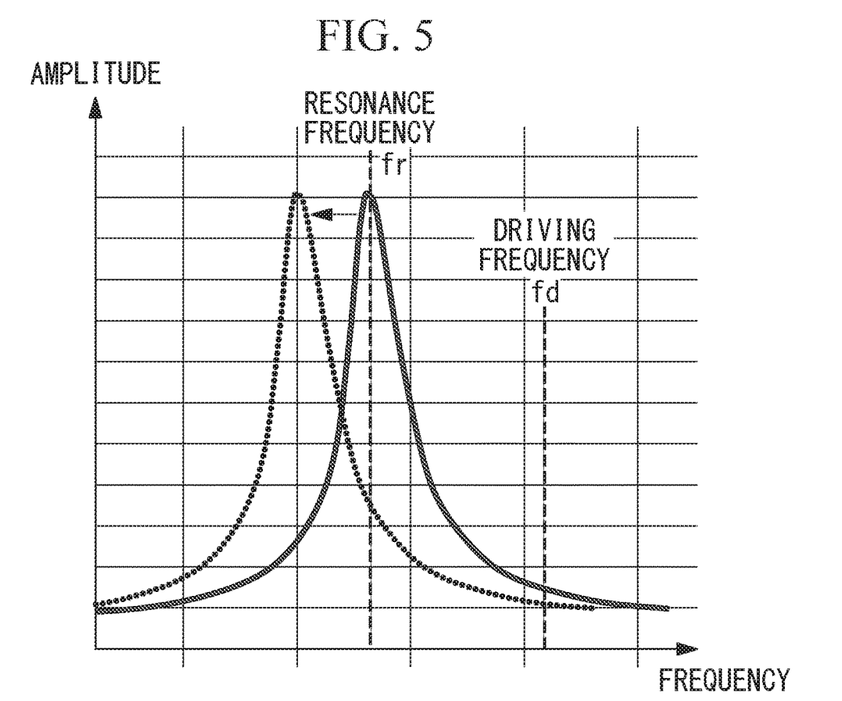
FIG. 5 is a diagram showing an example of the frequency characteristics of an oscillation amplitude of an optical fiber of the optical scanning apparatus in FIG. 2.

In other words, in this embodiment, as shown in FIG. 5, the driving frequency is set at a frequency different from the resonance frequency. By doing so, the occurrence of voids, where no trajectory is present in the vicinity of the center of the spiral trajectory, is reduced. In this case, in the case in which the resonance frequency is shifted, as indicated by a chain line, due to changes in the usage environment or the like, if the driving frequency is fixed, the oscillation amplitude fluctuates.

In the case of ideal oscillations, in other words, in the case in which the oscillations are not nonlinear oscillations, and also in the case in which the temporal change in a Q factor of the oscillations is small, the amplitude and the oscillation phase delay of the distal end of the optical fiber 7 are expressed as shown in Formula 1.

$$h_d = \frac{h_{max}}{\sqrt{\left(\frac{f_d}{f_r}\right)^2 + Q^2\left\{1-\left(\frac{f_d}{f_r}\right)^2\right\}^2}}$$ {Formula 1}

-continued $$\tan\theta_d = \frac{1}{Q}\frac{\left(\frac{f_d}{f_r}\right)}{1-\left(\frac{f_d}{f_r}\right)^2}$$

Here, fd is the driving frequency,
fr is the resonance frequency,
hd is the amplitude of the distal end of the optical fiber 7 at the driving frequency fd,
hmax is the amplitude of the distal end of the optical fiber 7 at the resonance frequency fr,
Q is the Q factor of the oscillations, and
θd is the oscillation phase delay of the distal end of the optical fiber 7 at the driving frequency.

The Q factor may be also expressed as Q=1/(2ξ) by using an attenuation factor of the oscillation of the optical fiber 7.

As is clear from Formula 1, the amplitude and the oscillation phase delay of the distal end of the optical fiber 7 at the driving frequency are determined by the ratio between the driving frequency and the resonance frequency. In this embodiment, even when the resonance frequency fluctuates, said resonance frequency is detected, and the driving frequency is adjusted so that the ratio becomes constant, and thus, the amplitude and the oscillation phase delay of the distal end of the optical fiber 7 at the driving frequency do not change, which makes it possible to scan the illumination light without causing any change in the trajectory.

Figure 6A:
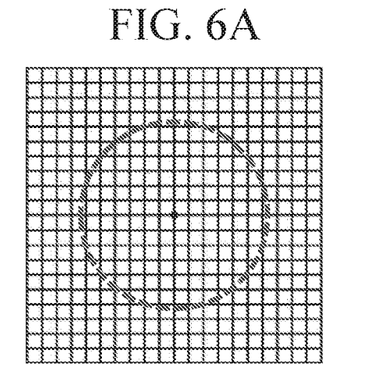
FIG. 6A is a diagram showing an example of an imaging subject observed with the scanning endoscope in FIG. 1.
Figure 6B:
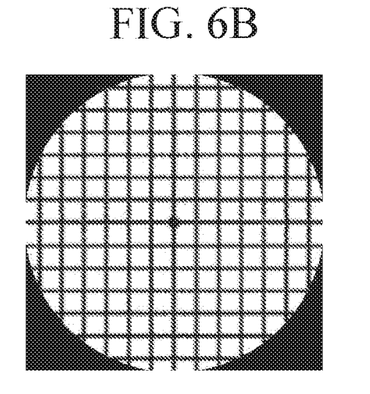
FIG. 6B is a diagram showing an image example of the imaging subject in FIG. 6A, the image being obtained by the scanning endoscope in FIG. 1, which operates at a reference resonance frequency and a reference driving frequency that are adjusted in advance.
Figure 6C:
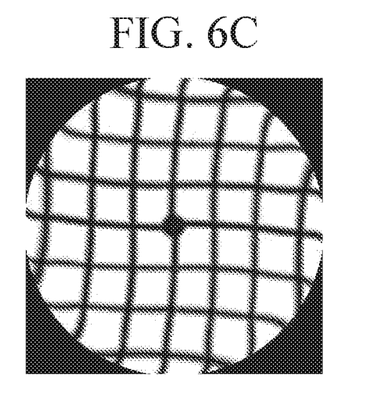
FIG. 6C is a diagram showing an image example of the imaging subject in FIG. 6A in the case in which observation is performed with a driving frequency that is fixed even when the resonance frequency fluctuates.

In other words, when a scanning range, indicated by a broken line, of the imaging subject A shown in FIG. 6A is scanned by using the reference resonance frequency and the reference driving frequency that are adjusted to the state at the time of factory shipment or when the apparatus is set up, in the case in which an image shown in FIG. 6B is obtained, if the driving frequency is fixed and the resonance frequency changes as shown in FIG. 5 due to variations in the usage environment, the amplitude of the distal end of the optical fiber 7 decreases, thus reducing the scanning range. As a result, as shown in FIG. 6C, the angle of view becomes narrow, and a distorted image is obtained.

Figure 6D:
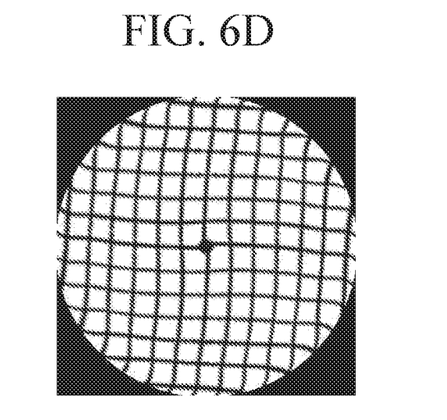
FIG. 6D is a diagram showing an image example of the imaging subject in FIG. 6A, the image being obtained by adjusting an angle of view by means of a driving voltage while the driving frequency is fixed.

In this case, by employing a method of increasing the driving voltage as a measure for recovering the amplitude of the distal end of the optical fiber 7, it is possible to ensure a sufficient angle of view, as shown in FIG. 6D; however, the image remains distorted.

Figure 6E:
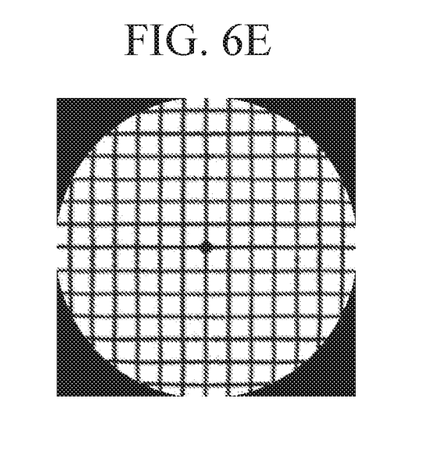
FIG. 6E is a diagram showing an image example of the imaging subject in FIG. 6A, the image being obtained in the case in which the driving frequency is adjusted so that the ratio of the driving frequency corresponding to the resonance frequency becomes constant.

In contrast, as with the optical scanning apparatus 3 according to this embodiment, by adjusting the driving frequency so that the ratio between the driving frequency and the resonance frequency becomes constant, the scanning trajectory does not vary, and thus, as shown in FIG. 6E, it is possible to obtain an image with no variation in the angle of view as well as less distortion.

As described above, with the optical scanning apparatus 3 and the scanning endoscope 1 according to this embodiment, there is an advantage in that, even when the resonance frequency fluctuates due to variations in the usage environment or the like, it is possible to effectively suppress variations in the angle of view and the occurrence of distortion.

In addition, in the case in which the amplitude hmax of the distal end of the optical fiber 7 at resonance also fluctuates at the same time, since the amplitude hd of the distal end of the optical fiber 7 at the driving frequency fd is proportional to hmax according to Formula 1, it is preferable that the fluctuation amount of hmax be detected, a driving voltage V be adjusted in proportion to the fluctuation amount, and the driving frequency be adjusted so that the ratio between the driving frequency and the resonance frequency becomes constant.

In order to detect the fluctuation amount of hmax, for example, because the fluctuation amount of hmax is proportional to the fluctuation amount of a current value output at the ADCs 23, 24 in FIG. 3, the proportional multiple thereof may be used as a detection value, and the driving voltage V may be adjusted accordingly.

Note that, in this embodiment, the drive unit 8 drives the optical fiber 7 in two directions orthogonal to each other, and thus, there are some cases in which fluctuation in the resonance frequency occurs in each drive direction.

In the case in which fluctuations in the resonance frequencies of the oscillations in the two directions do not significantly differ, and the frequency characteristics thereof are the same, the resonance-frequency detection unit 20 may detect only the resonance frequency of the oscillation in one direction and apply, for the driving in two directions, a single driving frequency to be calculated.

In addition, in the case in which fluctuations in the resonance frequencies in the two directions are substantially the same, the resonance frequencies in both directions may be detected, and a single driving frequency may be adjusted so that, as much as possible, the ratio between the driving frequency and the resonance frequency, in both directions, does not vary. Formula 2 below may be used as a method of calculating the driving frequency.

$$f'_d = f_d \times \frac{f'_x \cdot f'_y}{f'^2_x + f'^2_y} \cdot \left(\frac{f'_y}{f_x} + \frac{f'_x}{f_y}\right) \quad \{\text{Formula 2}\}$$

Here,
fd is the reference driving frequency,
fd' is a new driving frequency,
fx is the reference resonance frequency in the X-direction,
fx' is the resonance frequency in the X-direction after fluctuation,
fy is the reference resonance frequency in the Y-direction, and
fy' is the resonance frequency in the Y-direction after fluctuation.

Figure 8A:
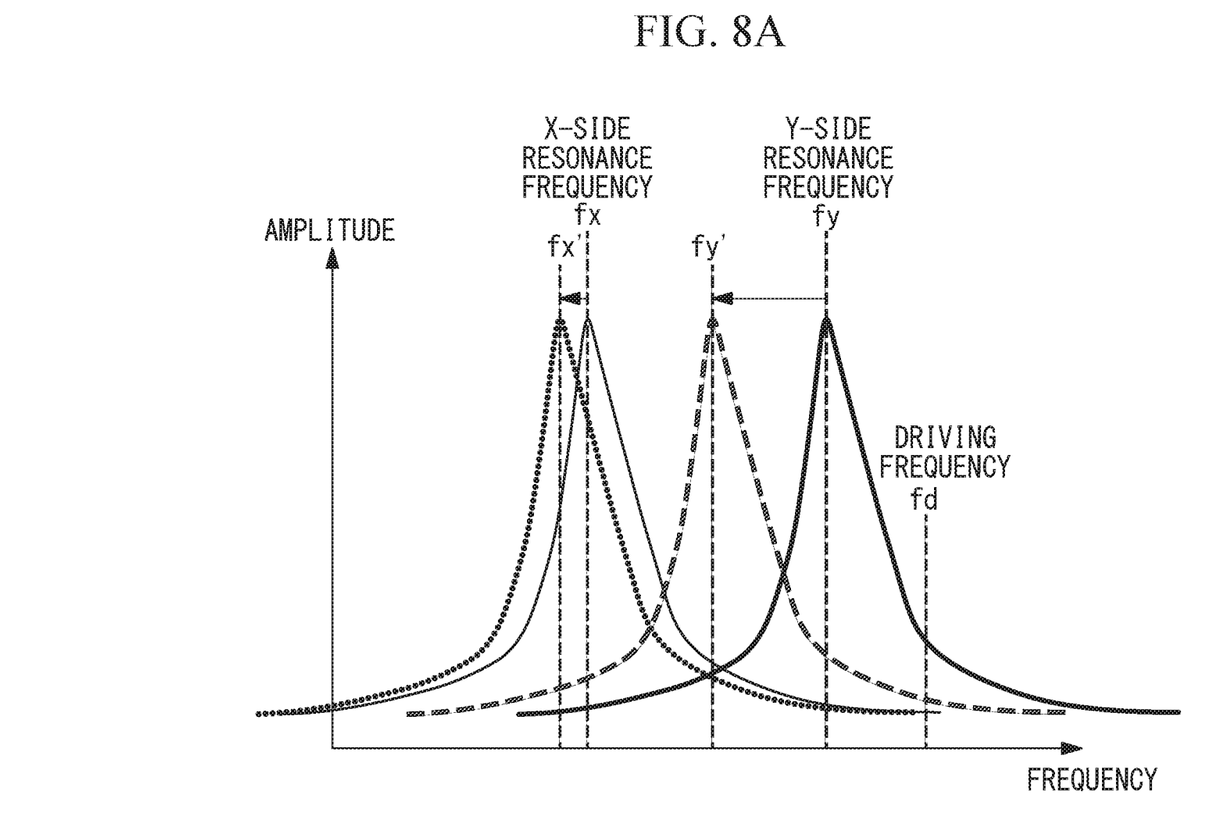
FIG. 8A is a diagram showing the frequency characteristics in the case in which a frequency difference between the resonance frequencies in two directions is originally large and there is a significant difference in the frequency fluctuation amount in each direction.

In addition, as shown in FIG. 8A, in the case in which a frequency difference between the resonance frequencies in the two directions is originally large, and there is a significant difference in the frequency fluctuation amount in each direction, only the fluctuation in the resonance frequency in the oscillating direction in which the ratio between the driving frequency and the resonance frequency is closer to 1 may be detected, and only the driving frequency of the oscillation in said direction may be adjusted. As shown in FIG. 8A, the slope of the graph of the frequency characteristics of the amplitude, at the original driving frequency fd, is larger in the oscillating direction in which the ratio is closer to 1 (Y-direction). Because of this, in the case in which the driving frequency and the resonance frequency are close to each other, if the driving frequency is fixed, the amplitude fluctuates by a large amount due to the fluctuation in the resonance frequency. Therefore, in this case, it is possible to suppress an amplitude fluctuation in the X-direction when the ratio between the resonance frequency in the Y-direction and the driving frequency is kept constant, which is more effective.

Figure 8B:
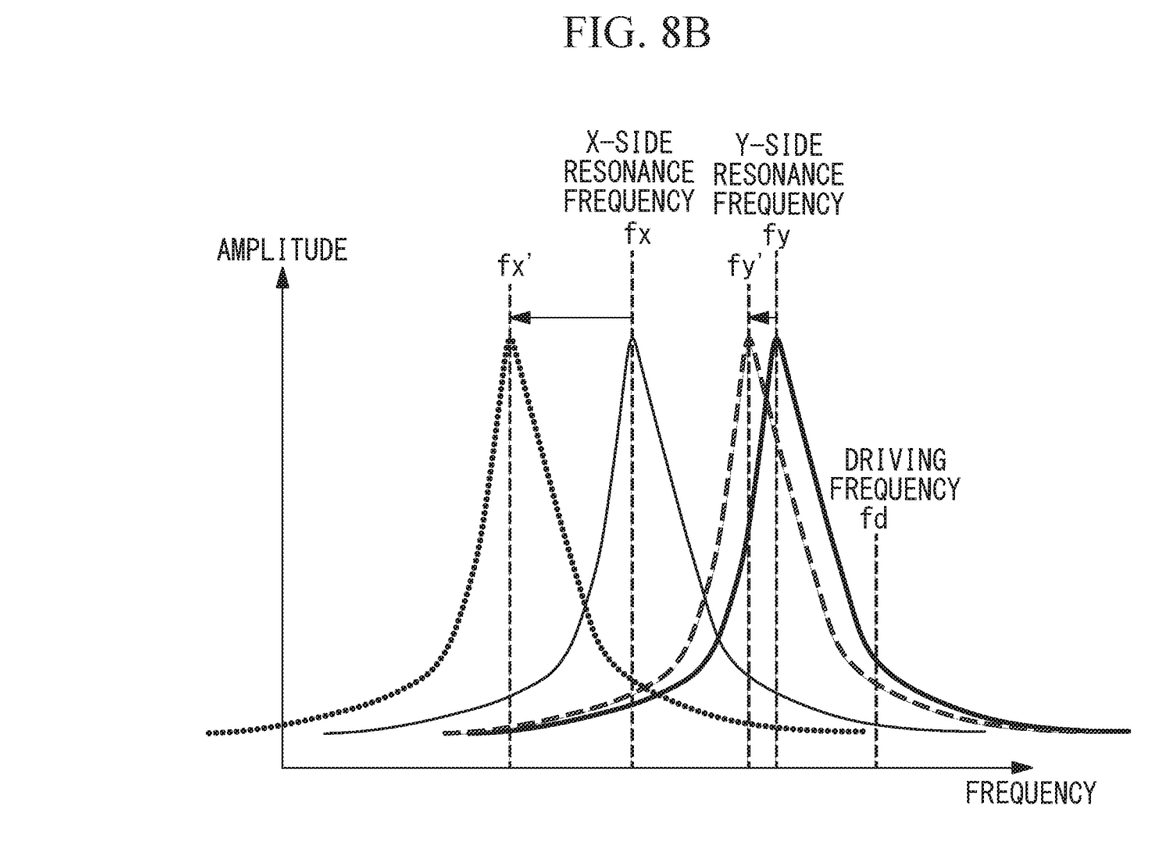
FIG. 8B is a diagram showing the frequency characteristics in the case in which the fluctuation amount of the resonance frequency in the oscillating direction in which the ratio between the driving frequency and the resonance frequency is away from 1 is extremely large compared to that of the other resonance frequency.

As shown in FIG. 8B, although the case in which the fluctuation amount of the resonance frequency in the oscillating direction in which the ratio between the driving frequency and the resonance frequency is farther from 1 is extremely large compared to that of the other resonance frequency may be assumed, such a situation is less likely to occur in practice, and thus, it suffices to consider the fluctuation in the resonance frequency in the oscillating direction in which the ratio is closer to 1.

In addition, in this case, it is preferable that new voltages Vx' and Vy', shown in Formula 3, be applied.

$$V'_x = \frac{\left(\frac{f'_d}{f'_x}\right)^2 - 1}{\left(\frac{f_d}{f_x}\right)^2 - 1} \times V_x \quad \{\text{Formula 3}\}$$

$$V'_y = \frac{\left(\frac{f'_d}{f'_y}\right)^2 - 1}{\left(\frac{f_d}{f_y}\right)^2 - 1} \times V_y$$

In addition, in this embodiment, the driving frequency may be adjusted in the case in which the fluctuation amount of the resonance frequency is larger than a prescribed threshold.

By doing so, the adjustment of the driving frequency is performed only in the case in which the resonance frequency has fluctuated beyond a prescribed threshold with respect to the reference resonance frequency, and thus, it is possible to prevent the driving frequency from being repeatedly adjusted due to minute fluctuations in the resonance frequency.

In addition, although the resonance frequency and the driving frequency at the time of factory shipment or the like have been illustrated as examples of the reference resonance frequency and the reference driving frequency, alternatively, a resonance frequency and a driving frequency that have been adjusted at an arbitrary point in time may be used as the reference resonance frequency and the reference driving frequency.

Figure 7A:
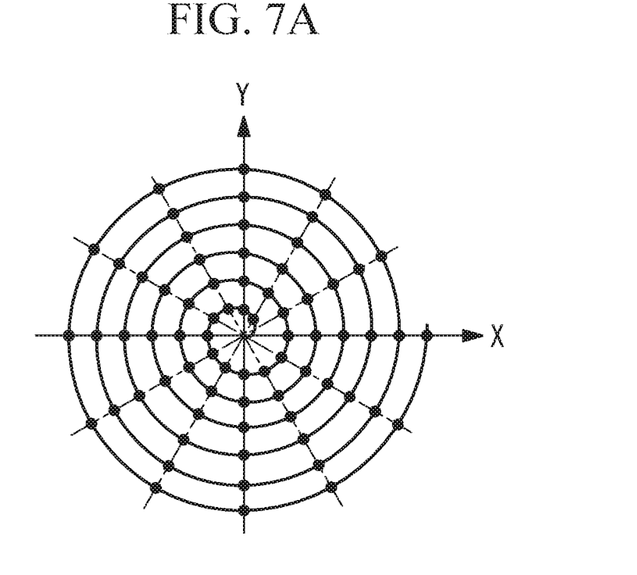
FIG. 7A is a diagram showing an example of sampling points in the case in which detection is performed at a prescribed sampling frequency.
Figure 7B:
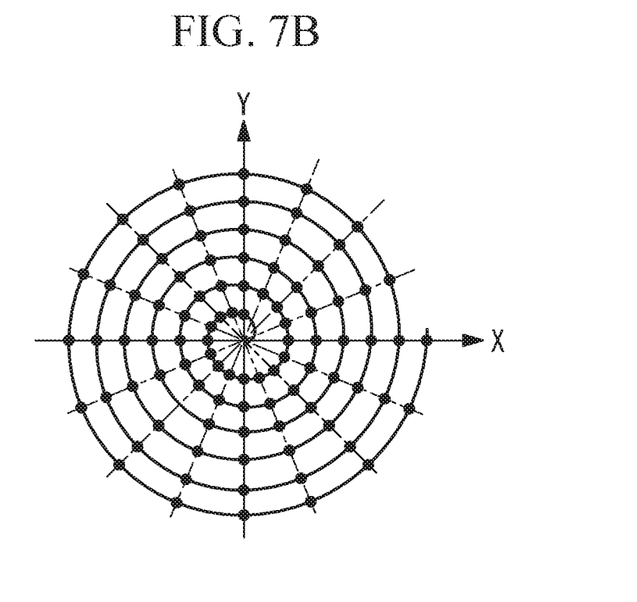
FIG. 7B is a diagram showing an example of sampling points in the case in which the driving frequency is adjusted so as to decrease and detection is performed at the same sampling frequency as in FIG. 7A.

In addition, in the case in which the driving frequency is changed so that the ratio between the driving frequency and the resonance frequency becomes constant, although there is no variation in the scanning trajectory, the scanning speed changes, and thus, the scanning positions to be sampled vary when the detection sampling frequency is constant. In the case in which a new driving frequency is lower than the reference driving frequency, because the scanning speed decreases, if the detection sampling frequency is constant, the number of sampling points on the scanning trajectory increases from a state shown in FIG. 7A to a state shown in FIG. 7B.

In the case in which the reference resonance frequency and the reference driving frequency are set at the time of factory shipment or the like and, in addition, the amount of phase delay is set to zero by means of calibration data, if the number of sampling points increases by changing the driving frequency, it is not possible to use the same calibration data as is.

In this case, any one of the following three processing methods may be employed.

The first method is a method in which the sampling frequency is also updated in accordance with a change in the driving frequency.

The sampling frequency fs' may be changed so that the ratio between the driving frequency fd' after adjustment and the sampling frequency fs' matches the ratio between the reference sampling frequency fs and the reference driving frequency fd at the time of factory shipment or the like.

In the second method, the scanning trajectory may be converted to a function from the calibration data, for example, with a method described in paragraph [0059] of WO 2015/125976, and the coordinates of the sampling positions after a change in the driving frequency may be calculated by performing arithmetic processing in which f=fd' is substituted in n=f×t, increasing in steps of t=1/fs.

With these methods, even in the case in which the ratio between the driving frequency and the resonance frequency is maintained constant, it is possible to correct image distortion without having to obtain the calibration data again.

The third method is a method that, instead of using calibration data, uses the fact that spots of light, on the imaging subject A, emitted from the distal end of the optical fiber 7 in the same oscillation phase are aligned in a row. With this method, image distortion may be corrected by using a function for the distortion correction amount adjusted on the basis of a shape of the row.

In addition, although the resonance-frequency detection unit 20 detects the resonance frequency on the basis of a phase difference between the current and the voltage applied to the piezoelectric elements 12a, 12b in this embodiment, alternatively, the current applied to the piezoelectric elements 12a, 12b may be measured while sweeping the frequency, thereby obtaining the frequency characteristics of the current value, and the resonance frequency value of the distal end of the optical fiber 7 may be measured by detecting the frequency at an extreme value in the obtained frequency characteristics.

In addition, although a scanning trajectory having a spiral shape is used in this embodiment, the shape thereof is not limited thereto and a scanning trajectory having another shape, for example, a raster shape or Lissajous shape may be used.

In the case of a raster shape or Lissajous shape, the condition is that a frame rate is equal to the magnitude of a difference between the X-direction driving frequency and the Y-direction driving frequency. Similarly, by performing control such that a value obtained by dividing the X-direction driving frequency by the X-direction resonance frequency is made constant and a value obtained by dividing the Y-direction driving frequency by the Y-direction resonance frequency is also made constant, it is possible to suppress the occurrence of image distortion due to changes in the environment.

In addition, in this embodiment, instead of the piezoelectric system in which the piezoelectric elements 12a, 12b are used, an electromagnetic system in which a magnet attached to the optical fiber 7 is made to vibrate by means of an electromagnetic coil, or another system may be used.

From the above-described embodiments, the following aspects of the present disclosure are derived.

An aspect of the present disclosure is an optical scanning apparatus including: an optical fiber that guides light from a light source to emit the light from a distal end thereof; a drive unit that causes the distal end of the optical fiber to oscillate at a driving frequency in a direction intersecting a longitudinal axis of the optical fiber; a resonance-frequency detection unit that detects a resonance frequency of the distal end of the optical fiber; and a driving-frequency adjustment unit that adjusts the driving frequency so that the ratio between the resonance frequency detected by the resonance-frequency detection unit and the driving frequency becomes constant.

With this aspect, when the light from the light source is made incident on the optical fiber, and the distal end of the optical fiber is oscillated at the driving frequency by actuating the drive unit, the light that is guided in the optical fiber and emitted from the distal end thereof is two-dimensionally scanned. In this case, the resonance-frequency detection unit detects the resonance frequency of the distal end of the optical fiber, and by using the detected resonance frequency, the driving-frequency adjustment unit adjusts the driving frequency so that the ratio between the resonance frequency and the driving frequency becomes constant.

As a result, a scanning trajectory of the light emitted from the distal end of the optical fiber is maintained constant even when the resonance frequency fluctuates due to changes in the usage environment, and it is possible to prevent variations in the scanning range.

In the abovementioned aspect, the drive unit may drive the distal end of the optical fiber in two directions orthogonal to each other, and the resonance-frequency detection unit may detect the resonance frequency in at least one of the drive directions.

By doing so, in the case in which the resonance frequencies in the two drive directions are substantially the same, it is possible to detect only the resonance frequency in one of the drive directions and use the detected resonance frequency to adjust the drive frequencies in two directions. In addition, in the case in which fluctuation in the resonance frequency in one direction is small, it is possible to detect only the resonance frequency in the other direction and adjust only the driving frequency in said other direction.

In addition, in the abovementioned aspect, the resonance-frequency detection unit may detect the resonance frequencies in the two drive directions, and the driving-frequency adjustment unit may adjust the driving frequency so that the ratio between the driving frequency and, among the two resonance frequencies detected by the resonance-frequency detection unit, the resonance frequency in the drive direction corresponding to the resonance frequency at which the ratio of the driving frequency thereto is closer to 1 becomes constant.

By doing so, even when the resonance frequency in the drive direction in which the ratio between the driving frequency and the resonance frequency is closer to 1 fluctuates, the driving-frequency adjustment unit adjusts the driving frequency in said direction. Because fluctuation in the amplitude associated with fluctuation in the resonance frequency increases as the ratio between the driving frequency and the resonance frequency become closer to each other, by adjusting the driving frequency in the drive direction in which the ratio between the driving frequency and the resonance frequency is closer to 1, it is possible to suppress fluctuations in the amplitude, thereby suppressing variations in the scanning trajectory.

In addition, in the abovementioned aspect, a storage unit that stores a reference resonance frequency and a reference driving frequency, which are set in advance, or the value of a ratio thereof may be provided, and the driving-frequency adjustment unit may adjust the driving frequency so that the ratio between the resonance frequency detected by the resonance-frequency detection unit and the driving frequency becomes equal to the value of the ratio stored in the storage unit.

By doing so, in the case in which the resonance frequency has fluctuated, for example, since the driving frequency is adjusted so that the ratio between the reference resonance frequency and the reference driving frequency, which are set in advance at the time of factory shipment or the like, is maintained, it is possible to prevent variations in the scanning trajectory that has been realized by the reference resonance frequency and the reference driving frequency.

In addition, in the abovementioned aspect, the driving-frequency adjustment unit may adjust the driving frequency when a difference between the resonance frequency detected by the resonance-frequency detection unit and the reference resonance frequency stored in the storage unit exceeds a prescribed threshold.

By doing so, the adjustment of the driving frequency is performed only in the case in which the resonance frequency has fluctuated beyond a prescribed threshold with respect to the reference resonance frequency, and thus, it is possible to prevent the driving frequency from being repeatedly adjusted due to minute fluctuation in the resonance frequency.

Another aspect of the present invention is a scanning endoscope provided with the abovementioned optical scanning apparatus.

According to the aforementioned aspects, an advantageous effect is afforded in that it is possible to reduce variations in the scanning range even when a resonance frequency fluctuates due to changes in the usage environment or the like.

REFERENCE SIGNS LIST

1 scanning endoscope
2 light source
3 optical scanning apparatus
7 optical fiber
8 driver
10 memory
16 controller (driving-frequency adjustor)
20 resonance-frequency detector

The invention claimed is:

1. An optical scanning apparatus comprising:
an optical fiber configured to guide light from a light source to emit the light from a distal end of the optical fiber;
an actuator configured to oscillate the distal end of the optical fiber at a driving frequency in a direction intersecting a longitudinal axis of the optical fiber; and
a controller comprising hardware, the controller being configured to:
detect a resonance frequency of the distal end of the optical fiber; and
adjust the driving frequency so that the ratio between the detected resonance frequency and the driving frequency becomes constant;
wherein:
the actuator is configured to drive the distal end of the optical fiber in two directions orthogonal to each other, and
the controller is configured to:
detect the resonance frequencies in the two drive directions,
adjust the driving frequency so that the ratio between the driving frequency and, among the detected two resonance frequencies, the resonance frequency in the drive direction corresponding to the resonance frequency at which the ratio of the driving frequency thereto is closer to 1 becomes constant, and
adjust the driving frequency when a difference between the detected resonance frequency and the reference resonance frequency stored in a memory exceeds a prescribed threshold.

2. An optical scanning apparatus comprising:
an optical fiber configured to guide light from a light source to emit the light from a distal end of the optical fiber;
an actuator configured to oscillate the distal end of the optical fiber at a driving frequency in a direction intersecting a longitudinal axis of the optical fiber;
a controller comprising hardware, the controller being configured to:
detect a resonance frequency of the distal end of the optical fiber;
adjust the driving frequency; and
a memory configured to store a reference resonance frequency and a reference driving frequency, which are set in advance, or the value of a ratio thereof,
wherein the controller is configured to:
adjust the driving frequency so that the ratio between the detected resonance frequency and the driving frequency becomes equal to the value of the ratio stored in the memory, and
adjust the driving frequency when a difference between the detected resonance frequency and the reference resonance frequency stored in the memory exceeds a prescribed threshold.

3. An optical scanning apparatus according to claim 2, wherein the actuator is configured to drive the distal end of the optical fiber in two directions orthogonal to each other, and
the controller is configured to detect the resonance frequency in at least one of the drive directions.

4. An optical scanning apparatus according to claim 3, wherein the controller is configured to:
detect the resonance frequencies in the two drive directions, and
adjust the driving frequency so that the ratio between the driving frequency and, among the detected two resonance frequencies, the resonance frequency in the drive direction corresponding to the resonance frequency at which the ratio of the driving frequency thereto is closer to 1 becomes constant.

* * * * *